(12) United States Patent
Yamato et al.

(10) Patent No.: US 7,608,250 B2
(45) Date of Patent: Oct. 27, 2009

(54) COSMETIC COMPOSITION

(75) Inventors: Naoya Yamato, Kawasaki (JP); Ryosuke Yumioka, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 814 days.

(21) Appl. No.: 11/244,001

(22) Filed: Oct. 6, 2005

(65) Prior Publication Data

US 2006/0029626 A1 Feb. 9, 2006

Related U.S. Application Data

(62) Division of application No. 10/357,354, filed on Feb. 4, 2003, now abandoned.

(30) Foreign Application Priority Data

Feb. 5, 2002 (JP) ............................. 2002-027659

(51) Int. Cl.
*A61Q 1/12* (2006.01)
*A61Q 5/00* (2006.01)
*A01N 37/52* (2006.01)

(52) U.S. Cl. .................. 424/69; 424/70.1; 424/400; 424/401; 514/634; 514/844; 514/880; 514/881

(58) Field of Classification Search ................ 424/400, 424/401, 440, 49, 54, 69, 70.1–74; 514/634, 514/844–848, 855–865, 880–881
See application file for complete search history.

(56) References Cited

U.S. PATENT DOCUMENTS 4,477,428 A 10/1984 Silbering et al.

6,974,582 B2 12/2005 Yamato
2003/0124156 A1 7/2003 Yamato

FOREIGN PATENT DOCUMENTS

EP 1 269 969 1/2003
JP 11228348 A 8/1999

*Primary Examiner*—Sreeni Padmanabhan
*Assistant Examiner*—Renee Claytor
(74) *Attorney, Agent, or Firm*—Oblon, Spivak, McClelland, Maier & Neustadt, L.L.P.

(57) ABSTRACT

A cosmetic composition for skin and/or hair, which comprises at least one kind of substance selected from the group consisting of an $N^\alpha,N^G$-di-acylarginine, for example, a compound represented by the following general formula (I):

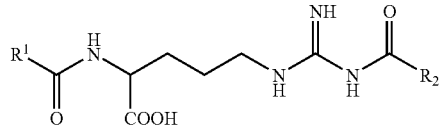

wherein $R^1$ and $R^2$ each independently represents a straight or branched-chain alkyl group having 1 to 21 carbon atoms or a straight or branched-chain alkenyl group having 2 to 21 carbon atoms. The cosmetic composition imparts much moistness and superior conditioning effects such as body or elasticity to hair, and to skin, said composition does not impart tackiness and blocked feeling, whilst imparts superior feeling of use such as moistness.

10 Claims, No Drawings

COSMETIC COMPOSITION

This application is a divisional of U.S. application Ser. No. 10/357,354, filed on Feb. 4, 2003, which claims priority to JP 2002-027659, filed on Feb. 5, 2002.

FIELD OF THE INVENTION

The present invention relates to a cosmetic composition for skin and/or hair. More specifically, the present invention relates to a cosmetic composition for skin and/or hair which comprises an $N^\alpha,N^G$-di-acylarginine.

RELATED ART

In cosmetics, polyhydric alcohols are used as moisturizers which impart moisture, softness and smoothness to the skin and hair. They are also used for the purpose of prevention of drying of final products or stabilization of emulsions in emulsified cosmetics.

In cosmetics for hair, in particular, polyhydric alcohols are used for the purposes of prevention of drying of hair after a shampoo and impartation of moistness to hair. However, in order to impart sufficient moistness, a large amount of polyhydric alcohols is needed to be formulated, and as a result, problems arise in that, for example, tackiness of hair is caused after drying, conditioning effects such as body or elasticity of hair cannot be sufficiently obtained, which results in inferior feeling of use. Moreover, polyhydric alcohols are formulated in cosmetics for skin for the purpose of improvement of moistness of skin after application of the cosmetics for skin. However, such cosmetics fail to provide sufficiently good feeling of use, for example, lubricity upon application is degraded, or tackiness or blocked feeling of skin is caused when a large amount of the substances are formulated.

Examples of other moisturizers include hydrophilic substances existing in cuticle and called NMF (Natural Moisturing Factor), saccharides and the like. However, the hydrophilic substances have problems in that they extremely change viscosity of cosmetics or they destroy emulsified state of emulsified cosmetics. Further, as for feeling of use, both of the hydrophilic substances and saccharides have problems in that they impart strong tackiness and blocked feeling to skin and hair, and thus they are poor in feeling of use.

As cosmetic compositions having superior conditioning effects such as moistness of hair and hair control and providing superior feeling such as no stiff feeling of skin, Japanese Patent Unexamined Publication (Kokai) Nos. (Hei)11-228527/1999 and (Hei)11-228348/1999 disclose cosmetic compositions containing one or more kinds of substances selected from mono-$N^\alpha$-long-chain acyl arginines and/or one or more kinds of powders subjected to a surface treatment with a mono-$N^\alpha$-long-chain acyl arginine. However, these cosmetic compositions do not impart satisfactory moistness to hair, and may cause stiffness when the component is formulated in a large amount. As also for skin, they do not impart satisfactory moistness, and fail to give sufficiently superior feeling of use, for example, they cause blocked feeling when the component is formulated in a large amount.

As a cosmetic composition imparting gloss and body to hair and skin, International Patent Publication WO/174305 discloses a cosmetic composition containing one or more kinds of substances selected from mono-$N^\alpha$-long-chain acyl arginines and/or powders subjected to a surface treatment with a mono-$N^\alpha$-long-chain acyl arginine together with a silicone compound for cosmetic use. However, this cosmetic composition also does not impart satisfactory moistness to hair, and may cause stiffness when the component is formulated in a large amount. As also for skin, the composition does not impart satisfactory moistness, and fails to give sufficiently superior feeling of use, for example, it causes blocked feeling when the component is formulated in a large amount.

DISCLOSURE OF THE INVENTION

An object of the present invention is to provide a cosmetic composition which solves the aforementioned problems. More specifically, the object of the present invention is to provide a cosmetic composition which imparts much moistness and superior conditioning effects such as body or elasticity to hair, and does not impart tackiness and blocked feeling to skin, but imparts superior feeling of use such as moistness.

The inventors of the present invention conducted various researches to achieve the foregoing object. As a result, they found that, when at least one kind of $N^\alpha,N^G$-di-acylarginine is formulated in a cosmetic composition, the aforementioned object was successfully achieved. They also found that, when at least one kind of $N^\alpha$-mono-long-chain acyl arginine or powder subjected to a surface treatment with at least one kind of $N^\alpha$-mono-long-chain acyl arginine was formulated in the aforementioned cosmetic composition, a further desirable cosmetic composition was obtainable. The present invention was achieved on the basis of the above findings.

The present invention thus provides a cosmetic composition for skin and/or hair, which comprises at least one kind of substance selected from the group consisting of an $N^\alpha,N^G$-di-acylarginine and a salt thereof. According to a preferred embodiment of the cosmetic composition, provided is the aforementioned cosmetic composition, wherein the $N^\alpha,N^G$-di-acylarginine is a compound represented by the following general formula (I):

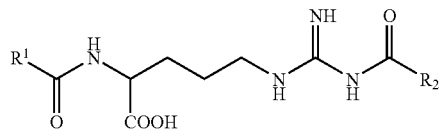

wherein $R^1$ and $R^2$ each independently represents a straight or branched-chain alkyl group having 1 to 21 carbon atoms or a straight or branched-chain alkenyl group having 2 to 21 carbon atoms. According to a further preferred embodiment, $R^1$ and $R^2$ each independently represents a straight or branched-chain alkyl group having 11 to 15 carbon atoms or a straight or branched-chain alkenyl group having 11 to 15 carbon atoms.

As another aspect of the present invention, provided is a cosmetic composition for skin and/or hair, which comprises the following components:

(A) at least one kind of substance selected from the group consisting of an $N^\alpha,N^G$-di-acylarginine and a salt thereof, and (B) at least one kind of substance selected from the group consisting of the following (a) and (b):

(a) an $N^\alpha$-mono-acylarginine and a salt thereof, (b) powder subjected to a surface treatment with at least one kind of substance selected from the group consisting of an $N^\alpha$-mono-acylarginine and a salt thereof. According to a preferred embodiment of the aforementioned invention, provided is the aforementioned cosmetic composition, wherein the $N^\alpha,N^G$-di-acylarginine is a compound represented by the general formula (I) mentioned above.

According to further aspects of the present invention, provided are use of at least one kind of substance selected from the group consisting of an $N^\alpha,N^G$-di-acylarginine and a salt thereof for manufacture of a cosmetic composition for skin and/or hair, and a moisturizer for skin and/or hair, which comprises at least one kind of substance selected from the group consisting of an $N^\alpha,N^G$-di-acylarginine and a salt thereof.

The cosmetic composition of the present invention provides no stiffness, whilst it provides superior conditioning effects such as moistness and body and elasticity, when applied as a composition for hair. Further, the cosmetic composition is characterized in that, when applied as a composition for skin, it provides no tackiness and no blocked feeling, whilst it provides excellent feeling of use such as moistness.

PREFERRED EMBODIMENTS OF THE INVENTION

Type of the $N^\alpha,N^G$-di-acylarginine contained in the cosmetic composition of the present invention is not particularly limited. Any compounds may be used wherein any fatty acid acyl groups bind respectively to the nitrogen atom in the α-amino group of the arginine and to the nitrogen atom of the terminal guanidine group of the arginine side chain. The aforementioned two fatty acid acyl groups may be the same or different. Any of L-, D-, or DL-arginine may be used. A salt of $N^\alpha,N^G$-di-acylarginine may be formulated in the cosmetic composition of the present invention. Type of the salt is not particularly limited. Base addition salts such as metal salts such as sodium salts, potassium salts, and calcium salts, organic amine salts, and ammonium salts, mineral acid salts such as hydrochlorides, sulfates, and nitrates, organic acid salts such as tartrates, citrates, acetates, methanesulfonates, and p-toluenesulfonates and the like may be used.

In the cosmetic composition of the present invention, a single kind of substance selected from the group consisting of an $N^\alpha,N^G$-di-acylarginine and a salt thereof may be used, or alternatively, two or more kinds of substances selected from the aforementioned group may be used in combination. Any stereoisomer of $N^\alpha,N^G$-di-acylarginine, any mixture of stereoisomers thereof, a racemate thereof and the like may be used for the cosmetic composition of the present invention. A hydrate or a solvate of $N^\alpha,N^G$-di-acylarginine or a salt thereof can also be used.

Preferred examples of the $N^\alpha,N^G$-di-acylarginine contained in the cosmetic composition of the present invention include $N^\alpha,N^G$-di-acylarginines represented by the aforementioned general formula (I). In the general formula (I), $R^1$ and $R^2$ each independently represents a straight or branched-chain alkyl group having 1 to 21 carbon atoms or a straight or branched-chain alkenyl group having 2 to 21 carbon atoms. $R^1$ and $R^2$ may be the same or different. Number of double bonds contained in the alkenyl group is not particularly limited. When two or more of double bonds are contained, they may be conjugated or non-conjugated double bonds. Further, the alkenyl group may contain one or more triple bonds. Among those groups, $R^1$ and $R^2$ may preferably be independently a straight or branched-chain alkyl group having 11 to 15 carbon atoms or a straight or branched-chain alkenyl group having 11 to 15 carbon atoms. Any of D-, L-, or DL-arginine may be used.

As a salt of the $N^\alpha,N^G$-di-acylarginine represented by the aforementioned general formula (I), for example, metal salts such as sodium salts, potassium salts, and calcium salts, base addition salts such as organic amine salts and ammonium salts, mineral acid salts such as hydrochlorides, sulfates, and nitrates, organic acid salts such as tartrates, citrates, acetates, methanesulfonates, and p-toluenesulfonates and the like may be used. In the cosmetic composition of the present invention, a single kind of substance selected from the group consisting of an $N^\alpha,N^G$-di-acylarginine represented by the aforementioned general formula (I) and a salt thereof may be used, or alternatively, two or more kinds of substances selected from the aforementioned group may be used in combination. Any stereoisomer of $N^\alpha,N^G$-di-acylarginine represented by the aforementioned general formula (I), any mixture of stereoisomers thereof, a racemate thereof and the like may be used for the cosmetic composition of the present invention. A hydrate or a solvate of the $N^\alpha,N^G$-di-acylarginine represented by the aforementioned general formula (I) or a salt thereof may also be used.

Specific examples of the $N^\alpha,N^G$-di-acylarginine represented by the general formula (I) include, for example, $N^\alpha,N^G$-di-acetylarginine, $N^\alpha,N^G$-di-propionylarginine, $N^\alpha,N^G$-di-2-ethylhexanoylarginine, $N^\alpha,N^G$-di-isostearoylarginine, $N^\alpha,N^G$-di-oleoylarginine, $N^\alpha,N^G$-di-octanoylarginine, $N^\alpha,N^G$-di-decanoylarginine, $N^\alpha,N^G$-di-lauroylarginine, $N^\alpha,N^G$-di-myristoylarginine, $N^\alpha,N^G$-di-palmitoylarginine, $N^\alpha,N^G$-di-stearoylarginine, $N^\alpha,N^G$-di-octyldodecylarginine, $N^\alpha,N^G$-di-behenoylarginine, $N^\alpha,N^G$-di-coconut oil fatty acid acyl arginine, $N^\alpha,N^G$-di-palm kernel oil fatty acid acyl arginine, $N^\alpha,N^G$-di-tallow fatty acid acyl arginine and the like. However, the $N^\alpha,N^G$-di-acylarginines that can be used for the cosmetic composition of the present invention are not limited to these examples.

Among the $N^\alpha,N^G$-di-acylarginines exemplified above, $N^\alpha,N^G$-di-decanoylarginine, $N^\alpha,N^G$-di-lauroylarginine, $N^\alpha,N^G$-di-myristoylarginine, $N^\alpha,N^G$-di-palmitoylarginine, $N^\alpha,N^G$-di-stearoylarginine and $N^\alpha,N^G$-di-coconut oil fatty acid acyl arginine are preferred from a viewpoint that they impart moistness and conditioning effects such as body or elasticity to hair. Particularly preferred are $N^\alpha,N^G$-di-lauroylarginine, $N^\alpha,N^G$-di-myristoylarginine, and $N^\alpha,N^G$-di-palmitoylarginine. The $N^\alpha,N^G$-di-acylarginines that can be used for the cosmetic composition of the present invention can be easily obtained by a reaction of arginine with a fatty acid halide in a mixed solvent of water and acetone under an alkaline condition as described in U.S. Pat. No. 4,477,428.

An amount of the $N^\alpha,N^G$-di-acylarginine to be formulated in the cosmetic composition of the present invention is not particularly limited. The amount of the $N^\alpha,N^G$-di-acylarginine to be formulated can be suitably determined by those skilled in the art depending on conditions such as a type of the $N^\alpha,N^G$-di-acylarginine, as well as a purpose of use, desired properties and the like of the cosmetic composition. Generally, the $N^\alpha,N^G$-di-acylarginine may be used in an amount ranging from 0.0001 to 10% by weight based on the total weight of the cosmetic composition. The amount is more preferably 0.01 to 1% by weight, further preferably from 0.05 to 1% by weight, and most preferably from 0.1 to 1% by weight. When the amount is less than 0.0001% by weight, a desired effect may sometimes not be satisfactorily obtained, and when the amount is more than 10% by weight, residual feeling on skin or hair may become stronger when the composition is applied to skin or hair.

If necessary, at least one kind of substance selected from the group consisting of (a) an $N^\alpha$-mono-acylarginine and a salt thereof, and (b) powder subjected to a surface treatment with at least one kind of substance selected from the group consisting of an $N^\alpha$-mono-acylarginine and a salt thereof may be formulated in the cosmetic composition of the present invention. AtType of the $N^\alpha$-mono-acylarginine used for the cosmetic composition of the present invention is not particularly limited. Any compound may be used which has a fatty acid acyl group on the $\alpha$-amino group of the arginine. For example, a compound having a straight or branched fatty acid acyl group having 2 to 22 carbon atoms is preferred. The acyl group may contain one or more unsaturated bonds. As the arginine constituting the $N^\alpha$-mono-acylarginine, any of L-, D- or DL-arginine may be used.

As a salt of the $N^\alpha$-mono-acylarginine, for example, base addition salts such as metal salts such as sodium salts, potassium salts, and calcium salts, organic amine salts, and ammonium salts, mineral acid salts such as hydrochlorides, sulfates, and nitrates, organic acid salts such as tartrates, citrates, acetates, methanesulfonates, and p-toluenesulfonates and the like may be used. In the cosmetic composition of the present invention, a single kind of substance selected from the group consisting of an $N^\alpha$-mono-acylarginine and a salt thereof may be used, or alternatively, two or more kinds of substances selected from the aforementioned group may be used in combination. Any stereoisomer of $N^\alpha$-mono-acylarginine, any mixture of stereoisomers thereof, a racemate thereof and the like may be used for the cosmetic composition of the present invention.

A hydrate or a solvate of $N^\alpha$-mono-acylarginine or a salt thereof can also be used. Examples of the powder subjected to a surface treatment with at least one kind of substance selected from the group consisting of an $N^\alpha$-mono-long-chain acyl arginine and a salt thereof include powders such as talc subjected to a surface treatment with any one of the $N^\alpha$-mono-long-chain acyl arginines explained above and salts thereof. The powder subjected to a surface treatment with an $N^\alpha$-mono-long-chain acyl arginine or a salt thereof can generally be prepared by appropriately mixing crystals of an $N^\alpha$-mono-long-chain acyl arginine or a salt thereof and powder such as talc by using an ordinary means.

Types of powder to be subjected to the surface treatment are not particularly limited, so long as the powders are usable for cosmetics. Examples thereof include organic powders such as nylon powder, polyethylene powder, polymethyl methacrylate powder, polystyrene powder, styrene/acrylic acid copolymer resin powder, benzoguanamine resin powder, polytetrafluoroethylene powder, and cellulose powder, ultraviolet ray blocking powders such as trimethyl-sil-sesquioxane powder, silicone resin powder, talc, kaolin, mica, sericite, muscovite, phlogopite, synthetic mica, lepidolite, lithia mica, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, calcined calcium sulfate, calcium phosphate, apatite hydrofluoride, hydroxyapatite, ceramic powder, zinc myristate, calcium palmitate, aluminum stearate, boron nitride, titanium dioxide, zinc oxide, iron red, iron titanate, fine titanium oxide particles, acicular titanium oxide, spindle-shaped titanium oxide, rod-shaped titanium oxide, fine zinc oxide particles and scaly zinc oxide, pigments such as $\gamma$-iron oxide, yellow iron oxide, black iron oxide, carbon black, mango violet, cobalt violet, chromium oxide, cerium oxide, chromium hydroxide, cobalt titanate, ultramarine, iron blue, titanium oxide-coated mica, titanium oxide-coated mica, titanium oxide-coated bismuth oxychloride, bismuth oxychloride, aluminum powder, copper powder and Red No. 201, chlorophyll, $\beta$-carotene, $N^\epsilon$-lauroyllysine and the like.

An amount of mono-$N^\alpha$-acylarginine used for the surface treatment of powder is not particularly limited. Generally, the amount may preferably be 0.01 to 30% by weight, more preferably 0.1 to 15% by weight, further preferably 0.5 to 5% by weight, based on the weight of the powder to be treated. When the amount is less than 0.01% by weight, improvements of gloss, agreeableness of cosmetics for skin and the like may become sometimes insufficient, and when the amount is more than 30% by weight, characteristic properties of powder for cosmetics itself may sometimes be lost.

$N^\alpha$-mono-long-chain acyl arginines and powders subjected to the surface treatment with an $N^\alpha$-mono-long-chain acyl arginine are specifically disclosed in Japanese Patent Unexamined Publication (KOKAI) Nos. (Hei)11-228527/1999 and (Hei)11-228348/1999. Those skilled in the art can easily produce an $N^\alpha$-mono-long-chain acyl arginine and powder subjected to the surface treatment with an $N^\alpha$-mono-long-chain acyl arginine by referring to the aforementioned patent documents and mix the same in the cosmetic composition of the present invention. The entire disclosures of the aforementioned patent documents are incorporated in the disclosures of the specification by reference.

Examples of the $N^\alpha$-mono-long-chain acyl arginine which can be suitably used for the cosmetic composition of the present invention include, for example, $N^\alpha$-mono-acetylarginine, $N^\alpha$-mono-propionylarginine, $N^\alpha$-mono-2-ethylhexanoylarginine, $N^\alpha$-mono-isostearoylarginine, $N^\alpha$-mono-oleoylarginine, $N^\alpha$-mono-octanoylarginine, $N^\alpha$-mono-decanoylarginine, $N^\alpha$-mono-lauroylarginine, $N^\alpha$-mono-myristoylarginine, $N^\alpha$-mono-palmitoylarginine, $N^\alpha$-mono-stearoylarginine, $N^\alpha$-mono-octyldodecylarginine, $N^\alpha$-mono-behenoylarginine, $N^\alpha$-mono-coconut oil fatty acid acyl arginine, $N^\alpha$-mono-palm kernel oil fatty acid acyl arginine, $N^\alpha$-mono-tallow fatty acid acyl arginine and the like. Among them, $N^\alpha$-mono-decanoylarginine, $N^\alpha$-mono-lauroylarginine, $N^\alpha$-mono-myristoylarginine, $N^\alpha$-mono-palmitoylarginine, $N^\alpha$-mono-stearoylarginine, and $N^\alpha$-mono-coconut oil fatty acid acyl arginine are preferred from a viewpoint of preferred feeling of use. $N^\alpha$-mono-lauroylarginine, $N^\alpha$-mono-myristoylarginine, $N^\alpha$-mono-palmitoylarginine, and $N^\alpha$-mono-stearoylarginine are preferred from a viewpoint that they are excellent in ability to impart moistness and conditioning effects such as body or elasticity to hair. Particularly preferred examples include $N^\alpha$-mono-lauroylarginine, $N^\alpha$-mono-myristoylarginine and $N^\alpha$-mono-palmitoylarginine.

In the cosmetic composition of the present invention, a formulation ratio of (A) at least one kind of substance selected from the group consisting of an $N^\alpha,N^G$-di-acylarginine and a salt thereof and (B) at least one kind of substance selected from the group consisting of (a) an $N^\alpha$-mono-acylarginine and a salt thereof and (b) powder subjected to a surface treatment with at least one kind of substance selected from the group consisting of an $N^\alpha$-mono-acylarginine and a salt thereof is not particularly limited. The ratio can be suitably determined by those skilled in the art depending on conditions such as types of $N^\alpha,N^G$-di-acylarginine and $N^\alpha$-mono-acylarginine, as well as a purpose of use, desired properties and the like of the cosmetic composition. The aforementioned components (A) and (B) are usually used in a formulation ratio in the range of 100:0.1 to 0.1:100 percent by weight. The range of the formulation ratio is more preferably 100:0.1-1:100, and most preferably 100:0.1-5:100.

The cosmetic composition of the present invention can be used as a cosmetic composition for skin and/or hair. More specifically, the cosmetic composition of the present invention can be used as various cosmetics for hair such as shampoo, hair conditioner, hair conditioner-in shampoo, conditioning shampoo, hair lotion, hair conditioner, hair treatment agent, hair cream, hair spray, hair liquid, hair wax, hair water, hair styling agent, permanent wave agent, hair coloring agent, acidic hair coloring agent, and hair manicure, and various cosmetics for skin such as skin lotion, emulsified lotion, face wash, make-up remover, cleansing lotion, emollient lotion, nourishing cream, emollient cream, massage cream, cleansing cream, body-shampoo, hand-wash liquid soap, solid soap, shaving cream, cosmetics for suntan, deodorant powder, deodorant lotion, deodorant spray, make-up removing gel, moisture gel, moisturizing essence, UV-cut essence, shaving foam, white powder, foundation, lip color, cheek color, eye liner, eye shadow, eyebrow cosmetics, bath liquid, antiperspirant and the like.

The cosmetic composition of the present invention can be easily prepared by mixing components ordinarily used for cosmetic compositions, which are exemplified above, and at least one kind of substance selected from the group consisting of an $N^\alpha,N^G$-di-acylarginine and a salt thereof in a conventional manner, and, if necessary, further mixing at least one kind of substance selected from the group consisting of (a) an $N^\alpha$-mono-acylarginine and a salt thereof and (b) powder subjected to a surface treatment with at least one kind of substance selected from the group consisting of an $N^\alpha$-mono-acylarginine and a salt thereof.

Examples of the components commonly used for the production of cosmetic compositions include, for example, materials described in the Japanese Standards of Cosmetic Ingredients, Comprehensive Licensing Standards of Cosmetics by Category, the Japanese Standards of Quasi-Drugs, the Japanese Pharmacopoeia and the Japan's Specifications and Standards for Food Additives and the like such as surfactants including anionic surfactants, cationic surfactants, amphoteric surfactants and nonionic surfactants as well as waxes, vegetable oils, animal fats and oils, natural fat and oil derivatives, mineral fats and oils, lower and higher fatty acid esters, synthetic fats and oils such as N-acyl glutamic acid ester, polymer substances, alcohols, polyhydric alcohols, extracts, amino acids, nucleic acids, vitamins, hydrolyzed proteins and derivatives thereof, glyceryl oleate, enzymes, anti-inflammatory agents, antibacterial agents, antiseptics, antioxidants, ultraviolet absorbers, chelating agents, antiperspirants, oxidation dyes, pH modifiers, pearling agents, and moistening agents. Types and amounts of these components can be appropriately selected by those skilled in the art depending on conditions including a purpose of use, desired properties and the like of the cosmetic composition of the present invention so as not to degrade advantageous effects of the present invention.

Examples of the surfactants include, for example, anionic surfactants such as alkyl sulfate salts, alkyl phosphate salts, polyoxyethylene alkyl ether sulfate salts, polyoxyethylene alkyl phenyl ether sulfate salts, polyoxyethylene alkylcarboxylic acid salts, alkyl phenyl ether sulfonate salts, salts of alkyl sulfosuccinates and derivatives thereof, salts of alkyl sarcosine and derivatives thereof, N-alkyl-N-methyl-β-alanine salts, polyoxyethylene coconut oil fatty acid monoethanolamide sulfate salt, polyoxyethylene alkyl ether phosphate salts, long chain fatty acid ethyl ester sulfonate salts, N-acylamino acid salts including N-coconut oil fatty acid acyl glutamic acid salts, N-lauroylglutamic acid salts, N-myristoylglutamic acid salts, N-coconut oil fatty acid acyl aspartic acid salts, N-coconut oil fatty acid acyl glycine salts and N-coconut oil fatty acid acyl alanine salts and higher fatty acid salts; amphoteric surfactants such as carbobetaine-type amphoteric surfactants, amidobetaine-type amphoteric surfactants, sulfobetaine-type amphoteric surfactants, hydroxysulfobetaine-type amphoteric surfactants, amidosulfobetaine-type amphoteric surfactants, phosphobetaine-type amphoteric surfactants and imidazoline-type amphoteric surfactants; nonionic surfactants such as lecithin derivatives, propylene glycol fatty acid esters, glycerin fatty acid esters, polyoxyethylene glycerin fatty acid esters, polyglycerin fatty acid esters, sorbitan fatty acid esters, polyoxyethylene sorbitan fatty acid esters, polyoxyethylene sorbit fatty acid esters, polyoxyethylene alkyl phenyl formaldehyde condensates, polyoxyethylene castor oil, polyoxyethylene hydrogenated castor oil, polyoxyethylene sterols and derivative thereof, polyethylene glycol fatty acid esters, polyoxyethylene alkyl ethers, polyoxyethylene polyoxypropylene alkyl ethers, polyoxyethylene alkyl phenyl ethers, polyoxyethylene lanolin and derivatives thereof, polyoxyethylene beeswax derivatives, polyoxyethylene alkylamines, polyoxyethylene fatty acid amides, alkanolamides, sugar esters, polyoxyethylene hydrogenated castor oil pyroglutamic acid esters and polyoxyethylene glyceryl pyroglutamic acid esters; cationic surfactants such as quaternary ammonium salts, amidoamines, N-acylarginine ester salts, and N-[3-alkyloxy-2-hydroxypropyl]-L-arginine salts. Examples of the salts of anionic surfactants include sodium salts, magnesium salts, potassium salts, ammonium salts, diethanolamine salts, triethanolamine salts, arginine salts, lysine salts and the like. Although the formulation amount of the surfactants in the cosmetic composition of the present invention is suitably determined depending on type and desired properties of intended product and is not particularly limited, it is usually 0.01-99% by weight, preferably 0.1-95% by weight, with respect to the total weight of the composition.

EXAMPLES

The present invention will be explained more specifically with reference to examples. However, the scope of the present invention is not limited by these examples.

Reference Example 1

Synthesis of $N^\alpha,N^G$-di-lauroylarginine

L-Arginine (20 g) was added with acetone (200 ml), water (300 ml) and 5 N NaOH aqueous solution (200 ml) and fully dissolved. This solution was added with lauroyl chloride (50.2 g) dissolved in acetone (100 ml) and stirred at room temperature for 5 hours. This reaction solution was adjusted to pH 4.8 with glacial acetic acid (61.3 g) and 75% sulfuric acid and added with ice water (500 ml) to obtain slurry solution of white crystals. The resulting slurry was filtered, and the white crystals obtained were subjected to slurry washing in ice water (1 L). The slurry was filtered, and the crystals were washed with ice water (500 ml) and methanol (370 g). The crystals obtained were dried under reduced pressure to obtain white solid (53.8 g, yield: 87.1%).

Reference Example 2

Synthesis of $N^\alpha,N^G$-di-palmitoylarginine

L-Arginine (10 g) was added with acetone (100 ml), water (150 ml) and 5 N NaOH aqueous solution (100 ml) and fully dissolved. This solution was added with palmitoyl chloride (15.8 g) dissolved in acetone (50 ml) and stirred at room temperature for 15 minutes. This reaction solution was further added with palmitoyl chloride (15.8 g) dissolved in acetone (50 ml) and stirred at room temperature for 2 days. The reaction solution was adjusted to pH 7.0 with 75% sulfuric acid to obtain a slurry solution of white crystals. The resulting slurry was filtered, and the crystals were washed with ice water (500 ml) and methanol (370 g). The crystals obtained were dried under reduced pressure to obtain white solid (31.6 g, yield: 86.4%).

Reference Example 3

Synthesis of $N^\alpha$-mono-lauroyl-L-arginine

L-Arginine (1106 g) was added with isopropyl alcohol (6919 g) and water (2964 g), and added dropwise simultaneously with lauroyl chloride (1522 g, Nippon Oil & Fats Co., Ltd.) and 27 wt % NaOH aqueous solution over 2 hours with stirring, while pH and reaction temperature were maintained at 10.5 to 11.5 and 10 to 13° C., respectively. After ripening for 1 hour, the reaction mixture was warmed to 50° C. and adjusted to pH 3.8 with addition of concentrated hydrochloric acid for complete dissolution of the reaction product. Then, the reaction mixture was adjust to pH 6.0 with addition of 27 wt % NaOH aqueous solution to deposit crystals, and the slurry was gradually cooled to 10° C. with stirring. After cooling to 10° C., the slurry was washed with water (10 kg) and isopropyl alcohol (4.4 kg), and the crystals obtained were dried under reduced pressure to give scaly crystals of $N^\alpha$-mono-lauroyl-L-arginine (2081 g, yield: 92.3%).

Reference Example 4

Synthesis of $N^\alpha$-mono-lauroyl-L-arginine

L-Arginine (50 g) was added with t-butyl alcohol (315 g) and water (125 g). The reaction mixture was added dropwise with lauroyl chloride (69 g) and 27 wt % aqueous sodium hydroxide (50 g) over 1 hour and 20 minutes, while the system was maintained at 10 to 15° C. and pH 10 to 11. After the addition, the reaction mixture was warmed to 45° C., added with sulfuric acid (17 g) and uniformly dissolved. Then, the system was adjusted to pH 4.9 with further addition of 27 wt % aqueous sodium hydroxide. The deposited crystals were collected by filtration and washed with water to obtain white crystals (92 g, yield: 90%).

Reference Example 5

Surface Treatment of Talc with $N^\alpha$-lauroyl-L-arginine

Talc (5.0 g, e.g., MICROACE P-30, Nippon Talc) and the compound of Reference Example 3 (0.25 g) were mixed, and a surface treatment was performed by stirring and mixing the mixture twice each for 1 minute using a home mixer (IFM-150, IWATANI INTERNATIONAL) to obtain treated powder.

Test Example 1

Shampoos each having the compositions shown in Table 1 (amounts of ingredients are shown in weight % relative to the total weight of 100%) were prepared in a conventional manner and applied to hair bundles having washed with 1% aqueous sodium lauryl ether sulfate, and then the hair bundles were sufficiently rinsed with water. Sensory evaluation was performed by a panel of five experts for (a) moistness of hair, (b) body and elasticity of hair, and (c) stiffness after drying. For the evaluation, average values of scores according to the evaluation criteria shown below were calculated. An average value of 4 or higher was determined as good (○), 3 to 3.9 as normal (Δ), and 2.9 or less as poor (×). The evaluation results are shown in Table 1.

<Evaluation Criteria>

(a) Moistness after Drying

5: Much moistness

4: Moistness

3: Moderate

2: Slightly less moistness

1: No moistness (b) Body and Elasticity after Drying

5: Strong body and elasticity

4: Body and elasticity

3: Moderate

2: Slightly less body and elasticity

1: No body and elasticity (c) Lesser Degree of Stiffness after Drying

5: No stiffness

4: Little stiffness

3: Moderate

2: Slight stiffness

1: Stiffness

TABLE 1

|  | Examples | | | | Comparative Examples | | |
| --- | --- | --- | --- | --- | --- | --- | --- |
|  | 1 | 2 | 3 | 4 | 1 | 2 | 3 |
| $N^\alpha$-Lauroyl-L-arginine |  |  | 1 |  | 1 |  |  |
| $N^\alpha$-Palmitoyl-L-arginine |  |  |  | 1 |  | 1 |  |
| $N^\alpha,N^G$-Di-lauroyl-L-arginine | 1 |  | 0.1 |  |  |  |  |
| $N^\alpha,N^G$-Di-palmitoyl-L-arginine |  | 1 |  | 0.1 |  |  |  |
| Concentrated glycerin | 2 | 2 | 2 | 2 | 2 | 2 | 2 |
| Cationized cellulose (*1) | 0.2 | 0.2 | 0.2 | 0.2 | 0.2 | 0.2 | 0.2 |
| Sodium lauryl ether sulfate | 11 | 11 | 11 | 11 | 11 | 11 | 11 |
| Cocoamidepropylbetaine | 3 | 3 | 3 | 3 | 3 | 3 | 3 |
| Citric acid monohydrate | 0.05 | 0.05 | 0.05 | 0.05 | 0.05 | 0.05 | 0.05 |
| Water | Remainder | Remainder | Remainder | Remainder | Remainder | Remainder | Remainder |
| Moistness after drying | ○ | ○ | ○ | ○ | ○ | ○ | Δ |
| Body and tenaciousness after drying | ○ | ○ | ○ | ○ | ○ | ○ | X |
| Lesser degree of stiffness after drying | ○ | ○ | ○ | ○ | Δ | Δ | Δ |

(*1) JR-400, Amerchol

Test Example 2

Emulsions each having the compositions shown in Table 2 (amounts of ingredients are shown in weight % based on the total weight of 100%) were prepared and applied in a suitable amount to back of hands of a panel of 5 experts to perform sensory evaluation for (a) moistness after the application, (b) lesser degree of tackiness after the application, and (c) lesser degree of blocked feeling after the application. For the evaluation, average values of scores according to the evaluation criteria shown below were calculated. An average value of 4 or higher was determined as good (○), 3 to 3.9 as normal (Δ), and 2.9 or less as poor (×). The evaluation results are shown in Table 2.

<Evaluation Criteria>

(a) Moistness after Application

5: Much moistness

4: Moistness

3: Moderate

2: Slightly less moistness

1: No moistness (b) Lesser Degree of Tackiness after Application

5: No tackiness

4: Little tackiness

3: Moderate

2: Slight tackiness

1: Tackiness (c) Lesser Degree of Blocked Feeling after Application

5: No blocked feeling

4: Little blocked feeling

3: Moderate

2: Slight blocked feeling

1: Blocked feeling

TABLE 2

|  | Examples | | | | | Comparative Examples | | |
|---|---|---|---|---|---|---|---|---|
|  | 5 | 6 | 7 | 8 | 9 | 4 | 5 | 6 |
| $N^\alpha$-Lauroyl-L-arginine |  |  | 1 |  |  | 1 |  |  |
| $N^\alpha$-Palmitoyl-L-arginine |  |  |  | 1 |  |  | 1 |  |
| $N^\alpha$-Lauroyl-L-arginine-treated talc (mentioned in Reference Example 5) |  |  |  |  | 5 |  |  |  |
| $N^\alpha,N^G$-Di-lauroyl-L-arginine | 1 |  | 0.1 |  |  |  |  |  |
| $N^\alpha,N^G$-Di-palmitoyl-L-arginine |  | 1 |  | 0.1 | 0.05 |  |  |  |
| Carboxyvinyl polymer (*) (1 wt % aqueous solution) | 10 | 10 | 10 | 10 | 10 | 10 | 10 | 10 |
| NaOH (10 wt % aqueous solution) | 0.4 | 0.4 | 0.4 | 0.4 | 0.4 | 0.4 | 6.4 | 0.4 |
| Liquid paraffin | 8 | 8 | 8 | 8 | 8 | 8 | 8 | 8 |
| Cetanol | 1 | 1 | 1 | 1 | 1 | 1 | 1 | 1 |
| Glyceryl stearate | 2 | 2 | 2 | 2 | 2 | 2 | 2 | 2 |
| PEO(20) sorbitan monooleate | 4 | 4 | 4 | 4 | 4 | 4 | 4 | 4 |
| Propylene glycol | 3 | 3 | 3 | 3 | 3 | 3 | 3 | 3 |
| 1,3-Butylene glycol | 5 | 5 | 5 | 5 | 5 | 5 | 5 | 5 |
| Methyl paraben | 0.2 | 0.2 | 0.2 | 0.2 | 0.2 | 0.2 | 0.2 | 0.2 |
| Water | Remainder | Remainder | Remainder | Remainder | Remainder | Remainder | Remainder | Remainder |
| Moistness after use | ○ | ○ | ○ | ○ | ○ | ○ | ○ | X |
| Lesser degree of tackiness after use | ○ | ○ | ○ | ○ | ○ | Δ | Δ | Δ |
| Lesser degree of bloked feeling after use | ○ | ○ | ○ | ○ | ○ | Δ | Δ | ○ |

(*1) Carbopol 940, BF Goodrich

Preparation Example 1

Preparation of Shampoos

Hair shampoos each having the following compositions were prepared in a conventional manner. All of the prepared shampoos were found to give no stiffness, whilst to give superior conditioning effects such as moistness after drying and body and elasticity for hair.

TABLE 3

| Components | Examples 10 | 11 | 12 |
|---|---|---|---|
| $N^{\alpha}$-Lauroyl-L-arginine | 1 | | |
| $N^{\alpha}$-Palmitoyl-L-arginine | | 1 | |
| $N^{\alpha},N^{G}$-Di-lauroyl-L-arginine | 0.1 | | 1 |
| $N^{\alpha},N^{G}$-Di-palmitoyl-L-arginine | | 0.1 | |
| Glycerin | 2 | | 2 |
| 1,3-BG | | 2 | |
| Sodium lauryl ether sulfate | 10 | 10 | 10 |
| Coconut oil fatty acid diethanolamide | 3 | 3 | 3 |
| Cationized cellulose (*1) | 0.1 | 0.1 | 0.1 |
| Dimethyldiallylammonium chloride/acrylamide copolymer (*2) | 0.3 | 0.3 | 0.3 |
| Anticeptic | Suitable amount | Suitable amount | Suitable amount |
| Water | Reminder | Reminder | Reminder |

(*1) Reoguard GP, Lion
(*2) Lipoflow MN, Lion

Preparation Example 2

Preparation of Hair Treatment Agents

Hair treatment agents each having the following composition were prepared in a conventional manner. All of the prepared hair treatment agents were found to give no stiffness, whilst to give superior conditioning effects such as moistness after drying and body and elasticity for hair.

TABLE 4

| Components | Examples 13 | 14 | 15 |
|---|---|---|---|
| $N^{\alpha}$-Lauroyl-L-arginine | 0.3 | | |
| $N^{\alpha}$-Palmitoyl-L-arginine | | 0.3 | |
| $N^{\alpha},N^{G}$-Di-lauroyl-L-arginine | 0.03 | | 0.3 |
| $N^{\alpha},N^{G}$-Di-palmitoyl-L-arginine | | 0.03 | |
| Glycerin | 3.0 | | |
| 1,3-BG | | 3.0 | |
| Sorbitol | | | 3.0 |
| Dimethylsiloxane/methyl(polyoxyethylene)siloxane copolymer (*1) | 3.0 | 3.0 | 3.0 |
| Liquid paraffin | 1.0 | 1.0 | 1.0 |
| Cetyl alcohol | 1.5 | 1.5 | 1.5 |
| Stearyl alcohol | 1.0 | 1.0 | 1.0 |
| Stearyltrimethylammonium chloride | 0.7 | 0.7 | 0.7 |
| Anticeptic | Suitable amount | Suitable amount | Suitable amount |
| Water | Reminder | Reminder | Reminder |

(*1) TSF4440, Toshiba Silicone

Preparation Example 3

Preparation of Hair Creams

Hair creams each having the following compositions were prepared in a conventional manner. All of the prepared hair creams were found to give no stiffness, whilst to give superior conditioning effects such as moistness after drying and body and elasticity for hair.

TABLE 5

| Components | Examples 16 | 17 | 18 |
|---|---|---|---|
| $N^{\alpha}$-Lauroyl-L-arginine | 1 | | |
| $N^{\alpha}$-Palmitoyl-L-arginine | | 1 | |
| $N^{\alpha},N^{G}$-Di-lauroyl-L-arginine | 0.1 | | |
| $N^{\alpha},N^{G}$-Di-palmitoyl-L-arginine | | 0.10 | 0.5 |
| Glycerin | 5 | 5 | 5 |
| Liquid paraffin | 15 | 15 | 15 |
| Vaseline | 15 | 15 | 15 |
| Breached beeswax | 2 | 2 | 2 |
| Carboxyvinyl polymer (*1) | 0.1 | 0.1 | 0.1 |
| Xanthan gum | 0.1 | 0.1 | 0.1 |
| Polyoxyethylene hydrogenated castor oil | 3 | 3 | 3 |
| Sodium hydroxide | 0.05 | 0.05 | 0.05 |
| Anticeptic | Suitable amount | Suitable amount | Suitable amount |
| Water | Reminder | Reminder | Reminder |

(*1) Carbopol 980, BF Goodrich

Preparation Example 4

Preparation of Skin Lotions

Skin lotions each having the following compositions were prepared in a conventional manner. All of the prepared skin lotions were found to give no tackiness and no blocked feeling, whilst to give excellent feeling of use such as moistness for skin.

TABLE 6

| Components | Examples 19 | 20 | 21 |
|---|---|---|---|
| $N^{\alpha}$-Lauroyl-L-arginine | 0.1 | | |
| $N^{\alpha}$-Palmitoyl-L-arginine | | 0.1 | |
| $N^{\alpha},N^{G}$-Di-lauroyl-L-arginine | 0.01 | | |
| $N^{\alpha},N^{G}$-Di-palmitoyl-L-arginine | | 0.01 | 0.1 |
| Propylene glycol | 1.0 | 1.0 | 1.0 |
| Hydroxypropylcellulose (*1) | 0.1 | 0.1 | 0.1 |
| Polyoxyethylene(15) glyceryl monostearate | 1.0 | 1.0 | 1.0 |
| Liquid paraffin | 0.2 | 0.2 | 0.2 |
| Anticeptic | Suitable amount | Suitable amount | Suitable amount |
| Water | Reminder | Reminder | Reminder |

(*1) HPC, Shin-Etsu Chemical

What is claimed is:

1. A method of moisturizing the skin of a subject in need thereof comprising applying to the skin of said subject a cosmetic composition comprising at least one kind of substance selected from an $N^{\alpha},N^{G}$-di-acylarginine or a salt thereof.

2. The method of claim 1, wherein the $N^\alpha,N^G$-di-acylarginine is a compound represented by formula (I):

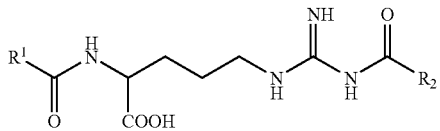

wherein $R^1$ and $R^2$ each independently represents a straight or branched-chain alkyl group having 1 to 21 carbon atoms or a straight or branched-chain alkenyl group having 2 to 21 carbon atoms or a salt thereof.

3. The method of claim 2, wherein $R^1$ and $R^2$ each independently represents a straight or branched-chain alkyl group having 11 to 15 carbon atoms or a straight or branched-chain alkenyl group having 11 to 15 carbon atoms.

4. A method of moisturizing the skin of a subject in need thereof comprising applying to the skin of said subject a cosmetic composition comprising:
   (A) at least one kind of substance selected from an $N^\alpha,N^G$-di-acylarginine or a salt thereof, and
   (B) at least one kind of substance selected from the group consisting of the following (a) and (b):
      (a) an $N^\alpha$-mono-acylarginine or a salt thereof,
      (b) powder subjected to a surface treatment with at least one kind of substance selected from the group consisting of an $N^\alpha$-mono-acylarginine or a salt thereof.

5. The method of claim 4, wherein the $N^\alpha,N^G$-di-acylarginine is a compound represented by formula (I):

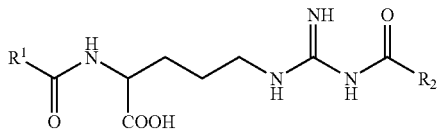

wherein $R^1$ and $R^2$ each independently represents a straight or branched-chain alkyl group having 1 to 21 carbon atoms or a straight or branched-chain alkenyl group having 2 to 21 carbon atoms or a salt thereof.

6. A method for washing hair, comprising applying to the hair of a subject in need thereof a composition comprising at least one kind of substance selected from an $N^\alpha,N^G$-di-acylarginine or a salt thereof, rinsing the hair, and drying the hair.

7. The method of claim 6, wherein the $N^\alpha,N^G$-di-acylarginine is a compound represented by formula (I):

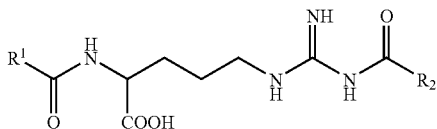

wherein $R^1$ and $R^2$ each independently represents a straight or branched-chain alkyl group having 1 to 21 carbon atoms or a straight or branched-chain alkenyl group having 2 to 21 carbon atoms or a salt thereof.

8. The method of claim 7, wherein $R^1$ and $R^2$ each independently represents a straight or branched-chain alkyl group having 11 to 15 carbon atoms or a straight or branched-chain alkenyl group having 11 to 15 carbon atoms.

9. A method for washing hair, comprising applying to the hair of a subject in need thereof a composition, rinsing the hair, and drying the hair wherein said composition comprises:
   (A) at least one kind of substance selected from an $N^\alpha,N^G$-di-acylarginine or a salt thereof, and
   (B) at least one kind of substance selected from the group consisting of the following (a) and (b):
      (a) an $N^\alpha$-mono-acylarginine or a salt thereof,
      (b) powder subjected to a surface treatment with at least one kind of substance selected from the group consisting of an $N^\alpha$-mono-acylarginine or a salt thereof.

10. The method of claim 9, wherein the $N^\alpha,N^G$-di-acylarginine is a compound represented by formula (I):

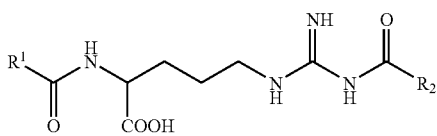

wherein $R^1$ and $R^2$ each independently represents a straight or branched-chain alkyl group having 1 to 21 carbon atoms or a straight or branched-chain alkenyl group having 2 to 21 carbon atoms or a salt thereof.

* * * * *